(12) United States Patent
Moreau et al.

(10) Patent No.: US 8,158,133 B2
(45) Date of Patent: Apr. 17, 2012

(54) PHARMACEUTICAL COMPOSITION USEFUL FOR VACCINES

(75) Inventors: Marinette Moreau, Saint-Germain (FR); Nicolas Osty, Luxeuil-les-Bains (FR)

(73) Assignee: Vetoquinol (FR)

(*) Notice: Subject to any disclaimer, the term of this patent is extended or adjusted under 35 U.S.C. 154(b) by 494 days.

(21) Appl. No.: 11/792,122

(22) PCT Filed: Dec. 1, 2005

(86) PCT No.: PCT/FR2005/002995
§ 371 (c)(1),
(2), (4) Date: Jul. 10, 2007

(87) PCT Pub. No.: WO2006/059009
PCT Pub. Date: Jun. 8, 2006

(65) Prior Publication Data
US 2008/0026006 A1    Jan. 31, 2008

(30) Foreign Application Priority Data
Dec. 2, 2004 (FR) ...................... 04 52838

(51) Int. Cl.
*A61K 45/00* (2006.01)
*A61K 39/00* (2006.01)
(52) U.S. Cl. .................. 424/283.1; 424/184.1
(58) Field of Classification Search .......... None
See application file for complete search history.

(56) References Cited

U.S. PATENT DOCUMENTS

| | | | |
|---|---|---|---|
| 4,788,056 A | 11/1988 | Lütticken et al. | |
| 5,688,761 A | 11/1997 | Owen et al. | |
| 5,744,137 A | 4/1998 | Stone | |
| 5,961,970 A | 10/1999 | Lowell et al. | |
| 6,303,662 B1 * | 10/2001 | Nagahama et al. | 424/522 |
| 6,919,442 B1 * | 7/2005 | Pavlakis et al. | 536/23.72 |
| 2003/0119774 A1 | 6/2003 | Foldvari et al. | |
| 2003/0175309 A1 | 9/2003 | Roberts et al. | |
| 2006/0292186 A1 * | 12/2006 | Garrigue et al. | 424/400 |

FOREIGN PATENT DOCUMENTS

| | | |
|---|---|---|
| EP | 0 296 661 A2 | 12/1988 |
| EP | 0 398 287 A1 | 11/1990 |
| EP | 0398287 | 11/1990 |
| EP | 0 781 559 A2 | 7/1997 |
| EP | 1 053 740 A1 | 11/2000 |
| EP | 1 469 009 A2 | 10/2004 |
| JP | 2000-256124 A | 9/2000 |
| JP | 2000-256132 A | 9/2000 |
| WO | WO 99/61003 A1 | 12/1999 |
| WO | WO 01/40240 A2 | 6/2001 |
| WO | 02/26209 | 4/2002 |
| WO | 03/002065 | 1/2003 |
| WO | WO 2004/087204 A2 | 10/2004 |

OTHER PUBLICATIONS

Lawrence et al. Microemulsion-based media as novel drug delivery systems. Advanced Drug Delivery Reviews, 2000, vol. 45, 89-121.*
Panayiotis P. Constantinides et al., "Formulation and Intestinal Absorption Enhancement Evaluation of Water-in-Oil Microemulsions Incorporating Medium-Chain Glycerides," Pharmaceutical Research, New York, NY, US, vol. 11, No. 10, 1994, pp. 1385-1390.
R.-M. Handjanni-Vila et B. Rondot, *Galenica 5 Les Systemes Disperses*, Puisieux F., Seiller M., Eds, 1983, vol. 5, pp. 195-219.
Raymond C. Rowe et al., "Handbook of Pharmaceutical Excipients", Fourth Edition, 2003.
Hoar et al., "Transparent Water-in-Oil Dispersions: the Oleopathic Hydro-Micell", *Nature*, 1943, vol. 152, p. 102.
L. M. Prince, "Microemuisions Versus Micelles," *Journal of Colloid and interface Science*, 1975, vol. 52, pp. 182-188.
L.M. Prince, "Microemuisions, Theory and Practice", Academic Press, NY 1977, Chap. 5, pp. 113-114.

* cited by examiner

Primary Examiner — Stacy B. Chen
(74) Attorney, Agent, or Firm — DLA Piper LLP (US)

(57) ABSTRACT

A pharmaceutical composition including at least a mixture of at least one oil, at least one surfactant and an aqueous phase, itself including at least one active substance, the pharmaceutical composition not being in the form of an emulsion, but in the form of an oily isotrope.

21 Claims, No Drawings

PHARMACEUTICAL COMPOSITION USEFUL FOR VACCINES

RELATED APPLICATION

This is a §371 of International Application No. PCT/FR2005/002995, with an international filing date of Dec. 1, 2005 (WO 2006/059009 A1, published Jun. 8, 2006), which is based on French Patent Application No. 04/52838, filed Dec. 2, 2004.

TECHNICAL FIELD

This disclosure concerns the field of pharmaceutical compositions, in particular, the field of vaccines. More precisely, the disclosure concerns a pharmaceutical composition useful as a vaccine (or vaccine composition) and a method for preparing the vaccine composition.

BACKGROUND

In the field of vaccines, it is well known that the efficacy of the vaccine composition is essentially due to the mixture of the antigen used with an adjuvant. Adjuvants for vaccines have been used for many years and are defined as compositions which, when combined with an antigen, produce an immune response greater than that of the antigen alone.

The immunogenic power of a vaccine without an adjuvant is weak as a rule, particularly when an inactivated virus is involved or when the antigen is simply a peptide or a protein and does not in itself make it possible to induce a protective response.

Extensive research has been performed to obtain satisfactory adjuvants which, ideally, ought to have the following properties:
  they induce a major immune response, particularly with a minimal antigen dose;
  they induce a mixed immune response (humoural and cellular) to promote and establish a memory response;
  they are perfectly tolerated and devoid of toxicity;
  they are, if possible, constituted of excipients commonly used in the pharmaceutical field, more specifically that of injectable drugs;
  they are easy to administer, with the aid of a syringe for example and if possible, to directly fill into ready-to-use syringes;
  they are easy to combine with various different antigens to allow standardization of production of different vaccines;
  they are easy to produce on an industrial scale using a manufacturing process which is easy to master;

A multitude of adjuvants of various different types and origins is known.

Alum (aluminium phosphate and hydroxide) is an adjuvant the use of which is widespread in human and veterinary vaccines.

Other adjuvants are known and used for research such as Freund's adjuvant constituted of a mixture of mineral oil and killed mycobacterium. This adjuvant is extremely effective and products pronounced immune responses. Its poor tolerance, however, limits its use to research in laboratory animals.

Various patents describe adjuvant compositions for vaccines.

U.S. Pat. No. 4,788,056 describes a combined vaccine against herpes and *E. coli* intended for vaccination of livestock. It mentions various different possible adjuvants, including oil/water emulsions or water/oil emulsions based on certain oils such as MIGLYOL® (medium-chain triglycerides) or surfactants such as polysorbate without, however, indicating any precise formulation of the adjuvant. Conventional emulsions are, however, involved in which the dispersed phase exists in the form of droplets. Furthermore, no indication is given with regard to the effect of the adjuvant on the immunogenic power of the vaccine.

U.S. Pat. No. 5,688,761 describes a water in oil microemulsion formulation which converts into an oil in water system by addition of an aqueous fluid, which results in release of the protein contained in the aqueous phase. The advantage of microemulsions is their spontaneous formation and their physical stability. The oils are well tolerated via the injectable route such as medium-chain mono and triglycerides. They are emulsified with the aqueous phase by means of the use of conventional surfactants known by one skilled in the art such as sorbitan esters or polysorbates. Their dilution by biological fluids during their injection results in inversion of the phases and, therefore, release of the biological agent incorporated in the aqueous phase. Certain examples of formulation show an increase in the activity of biological agents incorporated into the described formulation. However, the examples provided do not concern the field of vaccines.

U.S. Pat. No. 5,744,137 describes use of non-mineral oils in vaccines, in addition to vaccines in the form of water in oil emulsions containing a mixture of at least two surfactants chosen from among ethoxylated castor oil, propylene glycol laurate, propylene glycol caprylate and isosteryl diglyceryl succinate. The chosen oils are of animal or plant origin to limit in as far as possible the tissue reaction related to administration of poorly tolerated mineral oils.

U.S. Pat. No. 5,961,960 describes a vaccine adjuvant presented in the form of an oil in water submicroemulsion comprising an emulsifier (a phospholipid is involved), a non-ionic surfactant and an oil. The high cost of phospholipids restricts the applications of this invention however.

US 2003/0119774 describes a composition consisting of biphasic lipid vesicles allowing improvement of the immune response induced by an antigen.

US 2003/0175309 describes and adjuvant containing lecithin, an oil and an amphiphilic surfactant capable of forming a vaccine in the form of a stable oil in water emulsion which makes it possible to minimize local reactions in the infected animal.

WO 99/61003 describes a system for delivering active substances comprising a drug reserve in closely compacted solid form with an isotropic structure in the solid state. This system is adequate for delivering active substances by inhalation. The active substance comes in the form of liposomes, the liposomes being subsequently compacted to form the solid delivery system described.

EP 0 398 287 describes a pharmaceutical composition in the form of an isotropic solution consisting of one or several active substances and a medium which solidifies between 20° C. and 80° C. (particularly at ambient temperature) and is soluble in water.

The fact remains that there is a constantly recurrent need in the vaccine industry for new adjuvants presenting the properties listed above. In particular, the need remains to provide adjuvants allowing a major increase in the immunogenic power of the antigen. An advantage of such adjuncts adjuvants lies in the fact that they allow administration of low doses of antigen while retaining a satisfactory immune response.

It is particularly desirable to have such compositions available when the antigen is costly or difficult to produce in sufficient quantities or when a simple peptide or antigens obtained by synthesis or recombination is involved.

SUMMARY

We provide a pharmaceutical composition including at least a mixture of at least one oil, at least one surfactant and an aqueous phase, itself including at least one active substance, the pharmaceutical composition not being in the form of an emulsion, but in the form of an oily isotrope.

We also provide a method of preparing the composition including, during an initial stage, the antigen is dissolved or dispersed in the aqueous phase and the mixture is heated at a temperature of between about 30 and about 60° C.; during a second stage, which may be concomitant with the first, the surfactant or surfactants are mixed with the oil and the mixture is heated at a temperature of between about 30 and about 60° C.; during a third stage, the aqueous phase is incorporated in the oily phase using a homogenizer; and during a fourth stage, an oily isotrope obtained, cooled to ambient temperature and sterilized.

DETAILED DESCRIPTION

In a surprising and unexpected manner, we discovered that a pharmaceutical composition in the form of an oily isotrope, at least composed of a ternary mixture of oil/surfactant(s)/aqueous phase, the aqueous phase comprising the antigenic substance, is capable of having a markedly greater immunogenic power than a ternary composition of the former art in the form of an emulsion, in non-isotropic form. Furthermore, a composition in isotropic form may possess a viscosity compatible with administration by injection.

The term "isotrope" will be used hereafter to denote the oily isotrope, i.e. the isotropic ternary mixture of oil/surfactant(s)/aqueous phase. Likewise, "isotrope comprising an antigenic substance" will denote a composition in which the antigenic substance is included in the aqueous phase of the oily isotrope.

Oily isotrope means a mixture of oil, water and surfactants, the proportions of which are adjusted in such a manner that the preparation obtained is limpid, clear and has a low level of viscosity. In this manner, such a composition can be administered by injection. This type of composition corresponds to a dissolution of water in oil, or more specifically water in a micelle, itself being in oil (oily isotrope).

Indeed, during the constitution of the isotrope, molecular aggregates of surfactant form known as micelles, in which the active is more or less deeply inserted.

Isotropes are well known and can be found in Galenica, 1983, Vol. 5, chapter 5, page 195-219, for example. In particular, this work has water/oil/surfactant ternary diagrams, for example, a water/oil diagram of paraffin/Brij 96 on page 203, allowing determination of the respective concentrations of these compounds for which an isotropic system is obtained.

More specifically, a composition in isotropic form has a continuous three-dimensional structure, also known as a monophasic structure.

Emulsions for their part are formed of a system of two non-miscible liquids, one of which is finely divided into drops or vesicles, in the other. The dispersed phase is known as the internal or discontinuous phase and the dispersing phase is known as the external or continuous phase. An emulsion is, therefore, a liquid-liquid dispersion that possesses a biphasic structure.

A composition in isotropic form differs from an emulsion by the absence of organization of the vesicle type and by the presence of micelles.

"Organization of the vesicle type" means a structure having a wall comprising or constituted by components of the surfactant type, the wall including a volume comprising or constituted of a hydrophilic internal phase when the external phase is hydrophobic and vice-versa.

The results presented below and obtained in laboratory animals during trials with an isotrope comprising an antigenic substance showed that it was possible to obtain with such an isotrope a highly significant increase in the immunogenic activity of the antigen in comparison to the immunogenic activity obtained with the antigen in combination with a conventional adjuvant.

Furthermore, these trials showed that the isotrope outclassed preparations comprised of conventional water in oil emulsions.

We, therefore, provide a pharmaceutical composition comprising at least a mixture of at least one oil, at least one surfactant and an aqueous phase, itself comprising at least one active substance, the pharmaceutical composition being in the form of an oily isotrope. This composition is in isotropic form and, therefore, not in the form of an emulsion.

In particular, the composition has a viscosity compatible with administration by injection.

The active substance may be any type of biological active substance such as a living, attenuated or inactivated antigen. A living antigen signifies: a bacterium or a virus attenuated empirically or genetically, a proteinic (or glyco-lipoproteinic) antigen expressed in vivo by a vector (recombinant bacterium or virus). An inactivated antigen means a bacterium or virus inactivated either by physical methods or by chemical methods or a bacterial or viral extract, or a protein, a polypeptide or a peptide obtained by genetic recombination or by chemical synthesis, or at least an in vivo generator of a compounds comprising a sequence of amino acids.

Very specifically, the biological active substance may be inert.

The pharmaceutical composition may be a vaccine. In this form, the active substance is an antigen. The antigen may be of any origin and in any form commonly used in the field of vaccination. The antigen may, for example, be of viral, bacterial, parasitic or even tumoural origin.

The antigen may be natural or recombinant.

It may be composed of a microorganism (virus, bacteria or parasites), attenuated or inactivated if appropriate, or fractions, particularly acellular fractions, of said microorganism (purified antigens, native proteins or glycoproteins or peptides, polynucleotides, whether synthetic or produced by genetic engineering in particular), or indeed based on water-soluble or water-dispersible antigens.

Preferably, an antigenic phase composed of molecules excreted by the microorganism is used whether components of the bacterial wall or components of the cytoplasm.

The quantity of active substance and/or antigen in the composition is a function of the desired effect and the very nature of the active substance or the antigen used. One skilled in the art is capable of assaying the latter as a function of the active substance or antigen used.

The proportions of each of the constituents of the isotrope are adjusted so that the whole forms an oily isotrope.

More specifically, the surfactant concentration may be greater than the critical micelle concentration (CMC). For a concentration lower than the CMC, the essential portion of the surfactant is in monomer form. On the other hand, for a concentration above the CMC, there is an appreciable presence of micelles.

The CMC value may be determined by various different methods, for example, conductimetry or spectrophotometry, particularly as described in Dominguez et al., "Journal of Chemical Education", 1997, 1227-1231. In general, the CMC corresponds to a sudden change in the variation law of the parameter measured, for example the conductance or the absorbance.

Therefore, the compositions may comprise a surfactant content greater than or equal to the critical micelle concentration. This critical micelle concentration depends on several parameters including the nature of the components present in the composition and their content.

Therefore, the composition will comprise at least a high surfactant concentration and a low quantity of water.

The composition may comprise between about 10% to about 90% of oil, preferably about 40% to about 75% in weight, in relation to the weight of the total composition.

The quantity of water in the composition may be between about 0.5% and about 20%, preferably between about 3% and about 9% in weight, in relation to the weight of the total composition.

Finally, the quantity of surfactant in the composition may be between about 1% and about 60%, preferably between about 16% and about 45% in weight, in relation to the weight of the total composition.

The ratio of the quantity of water to the quantity of oil must not be less than 1 (quantity of oil equal to the quantity of water) and preferably should not be less than about 5 (quantity of oil at least 5 times greater than the quantity of water).

Many oils may be used in the composition. However, the oil must be compatible with pharmaceutical use, particularly injectable administration via the parenteral route.

The oil may be selected from among:
  mineral oils, such as and without limitation, paraffin oil, VASELINE® oil (i.e., petroleum jelly),
  non-mineral oils, such as cod liver oil, synthetic lipids, vegetable oils (such as, without limitation, soybean oil, olive oil, corn oil, peanut oil, cottonseed oil, sunflower oil, sesame oil, castor oil and almond oil), medium and long-chain triglycerides (such as the caprylic/capric acid triglycerides such as those sold by the Stearineries Dubois company or those sold under the names MIGLYOL 810®, 812® and 818® by the Dynamit Nobel company), terpenic oils such as squalane and squalene and
  mixtures thereof.

It is preferred to use an oil such as squalene or preferably an oil of the triglyceride family and very preferably medium-chain triglycerides of the MIGLYOL 810® type.

It is possible to use a mixture of oils.

The surfactants may be anionic, cationic, non-ionic or amphoteric.

The preferred class owing to its good safety, particularly during an injection, is that of the non-ionic surfactants. Preferably among the latter, all those usable via the injectable route may be used alone or in a mixture. It is possible to mention as an example and without it being possible to consider this list limitative, polysorbates, sorbitan esters, particularly esters of sorbitan and fatty acid, polyoxyethylenated derivatives of castor oil, polyoxyethylenated derivatives of stearic acid, copolymers of ethylene oxide and propylene oxide or poloxamers, esters of saccharose and fatty acid, esters of glycol and fatty acid, mono-, di-, tri-ester of fatty acid and glycerol, esters of polyethylene glycols and fatty acid and esters of saccharose and fatty acids.

Preferably, the polysorbates and sorbitan esters, particularly the esters of sorbitan and fatty acid are used.

It is possible to use a mixture of two or several surfactants. These surfactants may have identical or different HLB's (hydrophilic-lipophilic balance, which is a characteristic of the surfactants, related to the structure of their molecule).

Preferably, the surfactants have different HLB's to come near to the critical HLB of the oily phase used. The critical HLB is a function of the concentration of the emulsifiers and the chemical nature of the surfactants.

One skilled in the art will have no difficulty in finding in "Handbook of excipients", (Raymond C. Rowe, Paul J. Sheskey, Paul J. Weller-$4^{th}$ Edition, 2003), for example, the HLB's of the surfactants and will therefore be able to choose the suitable surfactant(s) according to the composition of the mixture to be produced.

The aqueous phase may contain, in addition to the water-soluble or water-dispersible antigen and water, other substances such as salts designed to complex the antigen in order to delay its release and therefore prolong its action. One may mention alumina silicate or calcium phosphate as examples of this type of salts.

The aqueous phase may also optionally contain non-specific immunogenic substances known in the trade such as lipopolysaccharides, or chitosan. Likewise, it may contain polymers, non-ionic polymers (such as poloxamer for example), synthetic clay (such as LAPONITE®, Chimilab Essor, for example), cytokins, or antioxidants such as vitamin E, recognized for their immunostimulant power.

The composition possesses a viscosity of between about 5 and about 150 mPa·s and preferably between about 5 and about 100 mPa·s.

The viscosity of the composition is measured at ambient temperature, preferably at 25° C., using rotor-stator-type viscosimeter, such as a Rhéo brand viscosimeter designated HAAK-VT500, according to the manufacturer's prescriptions.

The composition may be prepared by any operating method known in the art. For example, a composition may be prepared by the following operating method:
  during an initial stage, the antigen is dissolved or dispersed in the aqueous phase in which the above-described additional substances are optionally incorporated and the mixture is heated, on a water-bath, for example, at a temperature of between about 30 and about 60° C., preferably between about 35 and about 45° C.;
  during a second stage, which may be concomitant, the surfactant(s) are mixed with the oil and the mixture is heated, on a water-bath, for example, at a temperature of between about 30 and about 60° C., preferably between about 35 and about 45° C.;
  during a third stage, the aqueous phase is incorporated into the oily phase using a homogenizer (such as a RAYNERI® 33300 homogenizer). These devices are extensively used, particularly in preparation of emulsions and one skilled in the art will therefore have no difficulty in preparing the mixture; and
  during a final stage, the oily isotrope obtained is cooled to ambient temperature and sterilized. Various different processes described in the literature are usable for this operation, such as sterilization by heat, by ionizing radiation or by filtration for example. The preferred procedure is that of sterilizing filtration.

According to another method, it is also possible to use starting materials which are themselves sterile and conduct the entire manufacture in a clean room to avoid being obliged to resort to a final sterilization operation.

The following examples are give as illustrative and are not restrictive or limiting in any way. Other examples are possible using the same realization method.

Example 1

Composition of the Antigenic Phase

In the three examples below, the same aqueous phase containing the antigen is used. It involves an acellular antigenic phase composed of antigens excreted during culture of a bacterial strain of Streptococcus suis. This bacterium is responsible for a severe and highly widespread disorder in piglets.

The infection is characterized by nervous disorders (lack of motor coordination, trembling and convulsions) and joint disorders. Cases of septicaemia have also been reported, in addition to lung lesions. Transmission to humans is possible (abattoir workers, veterinary staff).

Only the acellular supernatant of the culture is used. A mixture of proteins is involved, one of which is used as an activity marker: MRP (Muramidase Released Protein), the titer of which may be determined by ELISA test (enzyme-linked immunosorbent assay). An anti-MRP monoclonal antibody is fixed in the wells of a microtitration plate. Following a saturation phase which makes it possible to avoid non-specific adsorption, the vaccine (containing the antigen to be assayed) is diluted and transferred to each well. After washing, a monoclonal antibody directed against the MRP protein and coupled to an enzyme is added. The reaction with the substrate/chromogen of the enzyme makes it possible to obtain a colored reaction measured using a plate reader. The intensity of the colorating is directly proportional to the quantity of antigen in the vaccine.

Once the titre of this primary solution has been obtained, one skilled in the art has no difficulty in adjusting by dilution (exceptionally by concentration) the titer of the solution which will be used in preparing the vaccines.

The aliquot of primary solution containing the desired quantity of antigens is diluted to necessary and sufficient quantity of a buffer commonly used in the field of vaccines, such as phosphate buffer for example.

Example 2

Composition 1

The following table presents the composition which is performed. The quantities are given in grams:

| | |
|---|---|
| Triglycerides (MIGLYOL 810 ®) | 51.50 |
| Polysorbate 80 (TWEEN 80 ®) | 14.95 |
| Sorbitan oleate (SPAN 80 ®) | 25.05 |
| Antigenic aqueous phase (prepared in example 1) | 8.50 |

The MIGLYOL 810®, TWEEN 80® and the SPAN 80® are mixed in a beaker. The oily phase obtained is heated on a water-bath at 40° C.

In parallel and separately, the aqueous phase is also heated on a water-bath at 40° C.

The aqueous phase is added to the oily phase dropwise, homogenizing with a turbine mixer (RAYNERI® 33300) rotating at 500 rpm.

During mixing the two beakers are kept at 40° C.

Once the mixture has been performed, it is removed from the water-bath and allowed to cool at ambient temperature.

The target MRP protein titre of the finished product is 1.6. The target titre is a titre relative to a reference antigen having a theoretical and arbitrary titre of 1. (1.6 means that the vaccine has a titre 1.6 times greater than the reference used).

Example 3

Composition 2

The following composition is prepared. The quantities are given in grams:

| | |
|---|---|
| Perhydrosqualene | 73.0 |
| Sorbitan oleate (SPAN 80 ®) | 8.4 |
| Ethoxylated sorbitan oleate (TWEEN 80 ®) | 9.6 |
| Antigenic aqueous phase (prepared in example 1) | 9.0 |

The process for preparing the mixture is identical to that described in example 2.

The target MRP protein titre of the finished product is 1.6.

Example 4

Composition 3

The following composition is prepared. The quantities are given in grams:

| | |
|---|---|
| Triglycerides (MIGLYOL 810 ®) | 51.50 |
| Polysorbate 80 (TWEEN 80 ®) | 25.05 |
| Sorbitan oleate (SPAN 80 ®) | 14.95 |
| Antigenic aqueous phase (prepared in example 1) | 8.50 |

The MIGLYOL 810®, TWEEN 80® and SPAN 80® are mixed in a beaker. This mixture is sterilized by heating to 120° C. for 30 minutes and subsequently allowed to cool at ambient temperature.

The aqueous phase containing the antigen is sterilized by filtration over a synthetic membrane with a porosity of 0.22 μm. The oily phase obtained above is heated in parallel and separately and the aqueous phase is prepared according to example 1 in a water-bath at 40° C.

Once the 2 phases are at the same temperature, the aqueous phase is added dropwise to the oily phase homogenizing with a turbine mixer (RAYNERI® 33300) rotating at 500 rpm.

During mixing, the two beakers are kept at the temperature.

Once the mixture has been prepared, it is removed from the water bath and allowed to cool at ambient temperature.

The target MRP protein titre of the finished product is 1.6.

Example 5

Comparison of the Immunogenic Activity of a Composition with the Immunogenic Activity of Conventional Formulations The activity of composition 1 of example 2 is compared with that of other compositions comprising an adjuvant or adjuvants described in the literature and known in the art.

Therefore, 4 other formulations (controls) are prepared according to the following compositions and operating methods:

Control formulation 1: conventional oil in water type emulsion:

For this emulsion, the same excipients described for the oily isotrope in example 2 were used in different proportions in order to obtain a very fine emulsion, for a critical HLB of 11. The quantities are given in grams.

| | |
|---|---|
| Medium-chain triglycerides (MIGLYOL 810 ®) | 20.0 |
| Polysorbate 80 (TWEEN 80 ®) | 9.4 |
| Sorbitan oleate (SPAN 80 ®) | 5.6 |
| Antigenic aqueous phase (prepared in example 1) | 65.0 |

The method used is the following:

The antigenic phase obtained in example 1 is sterilized by filtration over a synthetic membrane with a porosity of 0.22 μm.

The MIGLYOL®, TWEEN 80® and the SPAN 80® are mixed in a beaker and the mixture is sterilized by heating to 120° C. for 30 minutes and is allowed to cool at ambient temperature.

The aqueous phase (antigenic phase) and the oily phase are separately heated in a water-bath. Once the 2 phases are at the same temperature, the aqueous phase is added to the oily phase while stirring at 3000 rpm.

After addition of the aqueous phase, stirring is continued for 30 minutes.

Control formulation 2: oil in water commercial adjuvant (MONTANIDE® IMS, SEPPIC)

An adjuvant, MONTANIDE® IMS, sold by the SEPPIC company (PARIS, France), ready for use, was used in this second reference preparation. The quantities are given in grams.

| | |
|---|---|
| Aqueous phase containing the antigen (example 1) | 50.00 |
| MONTANIDE ® IMS | 50.00 |

The aqueous phase obtained in example 1 and the adjuvant are mixed while stirring for 20 seconds using the RAYNERI® T33300 homogenizer rotating at 150 rpm.

The whole is sterilized by filtration over a synthetic membrane with a porosity of 0.22 μm. Control formulation 3: commercial oil/water adjuvant (MONTANIDE® ISA 763 VG, SEPPIC)

Another adjuvant, MONTANIDE® ISA 763 VG, sold by the SEPPIC company (PARIS, FRANCE), ready for use, was used in this third reference formulation. The quantities are given in grams.

| | |
|---|---|
| Aqueous phase containing the antigen (example 1) | 30.00 |
| MONTANIDE ® ISA 763 VG | 70.00 |

The aqueous phase obtained in example 1 is filtered over a 0.22 μm nylon filter and the adjuvant over a PTFE filter with a porosity of 0.22 μm, the whole being assembled aseptically.

The adjuvant is transferred to a beaker while stirring at 800 rpm using a RAYNERI® T33300 homogenizer.

The antigenic aqueous phase is incorporated in a single operation, while stirring at 1200 rpm, maintained for 30 minutes.

Control formulation 4: water in oil commercial adjuvant (MONTANIDE® ISA 563 VG, SEPPIC)

Another adjunct adjuvant, MONTANIDE® ISA 563 VG, sold by the SEPPIC company (PARIS, FRANCE), ready for use, was used in this fourth reference formulation. The quantities are given in grams.

| | |
|---|---|
| Aqueous phase containing the antigen | 50.00 |
| MONTANIDE ® ISA 563 VG | 50.00 |

The aqueous part of the formulation is filtered over a 0.22 μm nylon filter and the adjuvant over a PTFE filter with a porosity of 0.22 μm, the whole being assembled aseptically.

The adjunct adjuvant is transferred to a beaker while stirring at 800 rpm using a RAYNERI® T33300 homogenizer. The antigenic aqueous phase is incorporated in a single operation, while stirring at 1200 rpm, maintained for 15 minutes.

Control formulation 5: LH adjuvant according to patent application WO 01/40240

Another adjuvant, LH, an experimental adjuvant of the COVACCINE company (Lelystadt, NETHERLANDS), ready for use, was used in this last reference formulation. The quantities are given in milliliters.

| | |
|---|---|
| Aqueous phase containing the antigen (example 1) | 25.00 |
| Saline buffer (PBS) | 25.00 |
| LH | 50.00 |

The aqueous adjuvant LH is sterilized by the supplier and received as is.

Aseptically, the aqueous antigenic phase and the saline buffer are mixed by magnetic stirring for 5 to 10 min. and the LH adjuvant is subsequently added very slowly ("in a trickle") to the antigenic phase-saline buffer mixture. Stirring is maintained for 10 min.

Comparison of the MRP Titres:

The MRP protein titers, measured as described above, of the reference formulations are approximately 4 (in RP units (Relative Potency: measurement unit by Relative Potency Calculation Software, version 3.0, US Department of Agriculture).

That of our composition is 1.01.

Indeed, given the small quantity of water present in the composition, it is not possible to incorporate as much antigen as in the reference formulations, except to increase its concentration in the aqueous phase, which could bias measurement of the immune response.

And yet, in spite of this markedly lower concentration and surprisingly, the results described below demonstrate a markedly greater immunogenic activity of our adjuvants.

Protocol of the Comparative Studies of the Immunogenic Activity and Tolerance of the Control Compositions and the Composition:

Comparison of the tolerance and immunogenic activity is performed in mice.

The immunogenic activity of the composition 1 in example 2 was compared with those of the Control compositions following the experimental protocol below:

BALB/C mice (supplier: Charles River) of 18-22 grams on reception received, with an interval of 2 weeks, 2 injections of 250 μl via the intraperitoneal route. The blood sample was taken one week after the recall, on autopsy of the mice. From a serological point of view, the anti-*Streptococcus suis* antibody level was assessed by the ELISA method.

The wells of a microplate are lined with the antigen (acellular supernatant of the culture) and subsequently saturated. The serums of the mice having received the vaccine are diluted and deposited in the plate. A marked anti-mouse antibody (conjugated with an enzyme) is added. The substrate/chromogen of the enzyme is deposited and the colored reaction is measured. The immunogenic activity of each composition is subsequently defined by a mean titer (in RP) corresponding to the mean of the titers of the mice constituting the group.

Tolerance is assessed according to three criteria: the mortality rate, the activity of the animal and the appearance of the hair coat. The presence of a residue at the injection site is also verified.

Results immunogenic power

The values indicated are relative: the value indicated represents the immunogenic power of a composition with reference to the immunogenic power of reference no. 5 which served as a reference for assessment of the immunogenic power of each reference tested.

| A | B | C | D | E | F |
|---|---|---|---|---|---|
| 26.8 | 0.60 | 0.33 | 15.33 | 8.53 | 1 |

A: Composition 1 according to the invention
B: Control 1
C: Control 2
D: Control 3
E: Control 4
F: Control 5

These results show that composition 1 (formula A) which contains 4 and 6 times less antigen than references 1 and 4, induces an immunological response between 2 and 80 times greater than that induced by these same controls.

tolerance in animals

| A | B | C | D | E | F |
|---|---|---|---|---|---|
| ++ | + | + | ± | ± | ++ |

++: Excellent (no signs)
+: good (no swelling, no residues of products, possibly ruffled hair coat)
±: poor (swelling, presence of residues of products, ruffled hair coat)

These results show that formula A (composition 1), exactly like reference formula F (composition 5), is perfectly tolerated both at a local and systemic level and much better tolerated than the 4 control formulas.

The invention claimed is:

1. A pharmaceutical composition consisting essentially of at least a mixture of at least one oil, at, least one surfactant and an aqueous phase, itself comprising at least one active substance, said pharmaceutical composition not being in the form of an emulsion, but in the form of an oily isotrope and wherein the water content of the pharmaceutical composition is between 3% and 9% and comprising 10% to 90% of oil, in relation to the weight of the total composition, and 1% to 60% of surfactant, in weight, in relation to the weight of the total composition.

2. The composition according to claim 1, having a viscosity compatible with administration by injection.

3. The composition according to claim 1, wherein the active substance is a biological active substance.

4. The composition according to claim 1, which is a vaccine.

5. The composition according to claim 1, wherein the active substance is an antigen.

6. The composition according to claim 1, wherein the antigen is of viral, bacterial, parasitic or tumoural origin.

7. The composition according to claim 5, wherein the antigen is natural or recombinant.

8. The composition according to claim 5, wherein the antigen is composed of a microorganism, optionally inactivated, or of fractions of the microorganism.

9. The composition according to claim 1, comprising at least a high surfactant concentration and a low water concentration.

10. The composition according to claim 1, having a ratio of the quantity of oil to the quantity of water not less than 1.

11. The composition according to claim 1, wherein the oil is selected from the group consisting of mineral oils, non-mineral oils, synthetic lipids, vegetable oils, medium and long-chain triglycerides, terpenic oils and mixtures thereof.

12. The composition according to claim 11, wherein the mineral oil is paraffin oil or petroleum jelly.

13. The composition according to claim 11, wherein the non-mineral oil is a vegetable oil selected from the group consisting of soy bean oil, olive oil, corn oil, peanut oil, cottonseed oil, sunflower oil, sesame oil, castor oil, almond oil and mixtures thereof.

14. The composition according to claim 11, wherein the medium and long-chain triglycerides are triglycerides of caprylic/capic acid.

15. The composition according to claim 11, wherein the terpenic oils are squalane or squalene.

16. The composition according to claim 1, comprising a mixture of oils.

17. The composition according, to claim 1, wherein the surfactant is selected from at least one of the group consisting of anionic, cationic, non-ionic and amphoteric surfactants.

18. The composition according to claim 17, wherein the surfactant is a non-ionic surfactant.

19. The composition according to claim 18, wherein the surfactant is selected from the group consisting of polysorbates, sorbitan esters, polyoxyethylenated derivatives of stearic acid, copolymers of ethylene oxide and propylene oxide or poloxamers, esters of saccharose and fatty acid, esters of glycol and fatty acids, mono-, di- and tri-esters of fatty acid and glycerol, esters of polyethylene glycols and fatty acids, esters of saccharose and fatty acids.

20. The composition according to claim 1, comprising a mixture of surfactants.

21. The composition according to claim 1, having a viscosity at ambient temperature between about 5 and about 150 mPa·s.

* * * * *